(12) United States Patent
Kamiyama et al.

(10) Patent No.: US 6,265,586 B1
(45) Date of Patent: Jul. 24, 2001

(54) PROCESS FOR PRODUCING INDOLMYCINS

(75) Inventors: Keiji Kamiyama, Ibaraki; Yutaka Nakayama, Nishinomiya, both of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/647,257

(22) PCT Filed: Apr. 8, 1999

(86) PCT No.: PCT/JP99/01872

§ 371 Date: Sep. 25, 2000

§ 102(e) Date: Sep. 25, 2000

(87) PCT Pub. No.: WO99/52905

PCT Pub. Date: Oct. 21, 1999

(30) Foreign Application Priority Data

Apr. 9, 1998 (JP) .................................................. 10-097177

(51) Int. Cl.⁷ .................................................. C07D 263/04
(52) U.S. Cl. ............................................................. 548/225
(58) Field of Search ............................................. 548/225

(56) References Cited

PUBLICATIONS

M. Preobrazhenskaya et al., "Total Synthesis of Antibiotic Indolmycin and its Stereoisomers", Tetrahedron, vol. 24, pp. 6131–6143(1968).

M. Schach von Wittenau et al., "Chemistry of Indolmycin", J. Am. Chem. Soc., vol. 85, pp. 3425–3431(1963).

H. Akita et al., "Formal Total Synthesis of (–)—Indolmycin", Chemical and Pharmaceutical Bulletin, vol. 38, No. 2, pp. 323–328(1990).

T. Takeda et al., "Asymmetric Total Synthesis of Indolmycin", Chemistry Letters, No. 2, pp. 163–166(1980).

*Primary Examiner*—Joseph K. McKane
*Assistant Examiner*—Joseph Murray
(74) *Attorney, Agent, or Firm*—Philippe Y. Riesen; Mark Chao

(57) ABSTRACT

A process for producing indolmycin or a salt thereof which comprises reacting a compound of the formula:

(II)

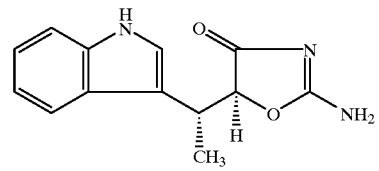

or a salt thereof with methylamine or a salt thereof, can be produced in an optically active form in a high yield and high quality, and is advantageous from the industrial point of view.

2 Claims, No Drawings

PROCESS FOR PRODUCING INDOLMYCINS

This application is the National Stage of International Application No. PCT/JP99/01872, filed on Apr. 8, 1999.

TECHNICAL FIELD

The present invention relates to a process for producing indolmycin which is useful as an antibacterial agent, especially as an anti-*Helicobacter pylori* agent.

BACKGROUND ART

Indolmycin can be produced by using producer strains *Streptomyces griseus* subsp. griseus ATCC12648 (American Type Culture Collection Catalogue of Bacteria & Bacteriophages], 18th edition, 1992), etc., in accordance with the method described, for example, in Antibiotics and Chemotherapy (Washington, D.C.), 10, 312 (1960) and in Antibiotics and Chemotherapy (Washington, D.C.), 10, 316 (1960). However, there are problems in that, in the method using microorganisms, the yield of the desired product is low and in that purification process is complicated. Though Indolmycin can be produced by using microorganisms as shown above, it can also be produced by chemical production methods. The production is shown in, for example, 1) Tetrahedron, 24, 6131 (1968) and 2) Chemistry Letters, 163 (1980), etc. In the method shown in the above literature 1), Indolmycin is produced through (−)-β-indolmycenic acid which is obtained by optical resolution of racemic β-indolmycenic acid, which is produced by using indole as starting material, with (+)-α-Phenylethylamine. However, in this method, the stereochemistry of the two asymmetric carbons contained in indolmycin is not controlled, and as a result, yield of the desired compound is low. The method shown in the above literature 2) involves many production steps and gives low yield of the desired product though stereochemistry is controlled in the method. As the production method of the racemate of indolmycin, there are known, for example, Journal of Organic Chemistry 51, 4920(1986), Tetrahedron Letters, 37, 6447(1996) ect,. Though there were fewer number of steps in this method, but optically active compounds were not obtained in this method.

DISCLOSURE OF INVENTION

After extensive investigation in view of the above problems, the present inventors found that indolmycin can be obtained as optically active compound in a high yield and that in the process stereochemistry of the two asymmetric carbons is controlled. The inventors conducted further investigation based on this finding, and developed the present invention. Thus the present invention is to provide a process for producing indolmycin, which has industrial advantages.

The present invention relates to:
(1) A process for producing a compound of the formula:

(I)

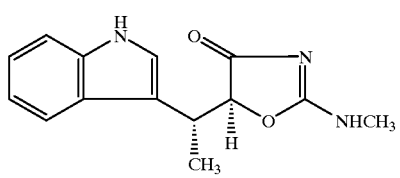

or a salt thereof, which comprises reacting a compound of the formula:

(II)

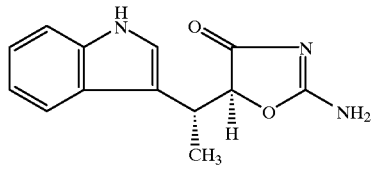

or a salt thereof with methylamine or a salt thereof.

(2) A process for producing a compound of the formula (II) or a salt thereof, which comprises reacting a compound of the formula:

(III)

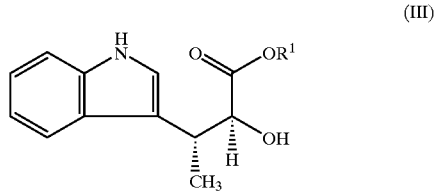

wherein $R^1$ is a hydrocarbon group which may be substituted, or a salt thereof with guanidine or a salt thereof in a secondary or tertiary alcohol, and (3) A process for producing a compound of the formula (I) or a salt thereof, which comprises reacting a compound of the formula (II) or a salt thereof, which is obtained by reacting a compound of the formula (III) or a salt thereof with guanidine or a salt thereof in a secondary or tertiary alcohol, with methylamine or a salt thereof.

In the above formula(III), as the "hydrocarbon group" in "hydrocarbon group which may be substituted" represented by $R^1$, there may be mentioned a chain aliphatic hydrocarbon group, an alicyclic hydrocarbon group and an aryl group, etc. Among them, a chain aliphatic hydrocarbon group is preferable.

The chain aliphatic hydrocarbon groups in the definition of hydrocarbon group include a straight chain or branched aliphatic hydrocarbon group such as an alkyl group, an alkenyl group, an alkynyl group, etc. Among them, lower alkyl groups, lower alkenyl groups, lower alkynyl groups, etc. are preferable, and lower alkyl groups are the most preferable. The lower alkyl groups include, for example, $C_{1-6}$alkyl such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl, 2-ethylbutyl, etc. Among them, $C_{1-3}$alkyl groups such as methyl, ethyl, propyl, etc. are preferable, and $C_{1-2}$alkyl groups such as methyl, ethyl are the most preferable. The lower alkenyl groups include $C_{2-6}$alkenyl such as vinyl, allyl, isopropenyl, 2-methylallyl, 1-propenyl, 2-methyl-1-propenyl, 2-methyl-2-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, etc. Among them, $C_{2-5}$alkenyl such as vinyl, allyl, isopropenyl, 2-methylallyl, 2-methyl-1-propenyl, 2-methyl-2propenyl, 3-methyl-2-butenyl, etc., are preferable. The lower alkynyl groups include $C_{2-6}$alkynyl such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, etc. Among them, $C_{2-4}$alkynyl such as ethynyl, 1-propynyl, 2-propynyl, etc. are preferable.

The alicyclic hydrocarbon groups in the definition of the hydrocarbon group may be saturated or unsaturated, and include cycloalkyl group, cycloalkenyl group, cycloalkadienyl group, etc. The cycloalkyl groups include ones having 3 to 9 carbon atoms such as cyclopropyl, cyclobutyl, cyclopentyl, cyclohexyl, cycloheptyl, cyclooctyl, cyclononyl, etc. Among them, $C_{3-6}$cycloalkyl groups such as cyclopropyl, cyclobutyl, cyclopentyl, cyclohexyl, etc. are preferable. The cycloalkenyl groups include $C_{3-6}$cycloalkenyl such as 2-cyclopentene-1-yl, 3-cyclopentene-1-yl, 2-cyclohexene-1-yl, 3-cyclohexene-1-yl, 1-cyclobutene-1-yl, 1-cyclopentene-1-yl, etc. The cycloalkadienyl groups include $C_{4-6}$cycloalkadienyl such as 2,4-cyclopentadiene-1-yl, 2,4-cyclohexadiene-1-yl, 2,5-cyclohexadiene-1-yl, etc.

The aryl groups in the definition of the hydrocarbon groups may be monocyclic or condensed aromatic hydrocarbon groups, and include ones having 6 to 12 carbon atoms such as phenyl, naphthyl, anthryl, phenanthryl, acenaphthylenyl, etc. Among them, ones having 6 to 10 carbon atoms such as phenyl, 1-naphthyl, 2-naphthyl, etc. are preferable.

The substituents in the definition of hydrocarbon groups which may be substituted, shown by $R^1$ include aryl groups which may be substituted(e.g. aryl having 6 to 12 carbon atoms such as phenyl, naphthyl, anthryl, phenanthryl, acenaphthylenyl, etc.), cycloalkyl groups which may be substituted (e.g. cycloalkyl having 3 to 9 carbon atoms such as cyclopropyl, cyclobutyl, cyclopentyl, cyclohexyl, cycloheptyl, cyclooctyl, cyclononyl, etc.), cycloalkenyl groups which may be substituted(e.g. $C_{3-6}$cycloalkenyl such as 2-cyclopentene-1-yl, 3-cyclopentene-1-yl, 2-cyclohexene-1-yl, 3-cyclohexene-1-yl, 1-cyclobutene-1-yl, 1-cyclopentene-1-yl, etc.), amino groups which may be substituted (e.g. alkylamino having 1 to 4 carbon atoms such as amino, methylamino, ethylamino, propylamino, etc., dialkylamino having 2 to 8 carbon atoms such as dimethylamino, methylethylamino, diethylamino, methylpropylamino, dipropylamino, etc.), hydroxyl group which may be substituted (e.g., hydroxyl group, alkoxy group having 1 to 4 carbon atoms such as methoxy, ethoxy, propoxy, etc. ), thiol group which may be substituted (e.g. mercapto, alkylthio having 1 to 4 carbon atoms such as methylthio, ethylthio, propylthio, etc. ), halogen (e.g., fluorine, chlorine, bromine, iodine), etc. The hydrocarbon group may be substituted with 1 or more, preferably one to three of these substituents at any position.

As the salts of the compounds of the formula (I), there may be mentioned acid addition salts. The acids which form the acid addition salts include inorganic acids such as hydrochloric acid, sulfuric acid, hydrogen bromide, hydrogen iodide, phosphonic acid, sulfamic acid, etc. and organic acids such as acetic acid, lactic acid, succinic acid, maleic acid, tartaric acid, citric acid, gluconic acid, ascorbic acid, benzoic acid, methanesulfonic acid, p-toluenesulfonic acid, cinnamic acid, fumaric acid, etc.

As the salts of the compounds of the formula (II), there may be mentioned the acid addition salts which are mentioned as the salts of the compound of the formula (I).

As the salts of methylamine, there may be mentioned acid addition salts. The acids which form acid addition salts include inorganic acids such as hydrochloric acid, sulfuric acid, hydrogen bromide, hydrogen iodide, phosphonic acid, sulfamic acid, etc., and organic acids such as acetic acid, lactic acid, succinic acid, maleic acid, tartaric acid, citric acid, gluconic acid, ascorbic acid, benzoic acid, methanesulfonic acid, P-toluenesulfonic acid, cinnamic acid, fumaric acid, etc.

As the salts of the compounds of the formula (III), there may be mentioned, when $R^1$ is not a hydrogen atom, acid addition salts which are mentioned as the salts of the compound of the formula (I), and when $R^1$ is a hydrogen atom, inner molecular salts, inorganic base salts and organic base salts. The inorganic base which forms to the inorganic base salt include alkali metals (for example, sodium, potassium, etc.), alkaline earth metals (for example, calcium, etc.), etc. The organic salt which forms the organic base salt includes, for example, triethylamine, diisopropylethylamine, pyridine, lutidine, procaine, 2-phenylethylbenzylamine, dibenzylethylenediamine, ethanolamine, diethanolamine, trishydroxymethylaminomethane, polyhydroxyalkylamine, N-methylglucosamine, etc.

The salts of guanidine include acid addition salts. The acids which form acid addition salts include inorganic acids such as hydrochloric acid, sulfuric acid, hydrogen bromide, hydrogen iodide, phosphonic acid, sulfamic acid, etc., and organic acids such as acetic acid, lactic acid, succinic acid, maleic acid, tartaric acid, citric acid, gluconic acid, ascorbic acid, benzoic acid, methanesulfonic acid, P-toluenesulfonic acid, cinnamic acid, fumaric acid, etc.

The reaction between the compound of the formula (II) or a salt thereof (sometimes hereinafter referred to as Compound (II)) and methylamine or a salt thereof is usually carried with or without a solvent. The solvents include water, alcohol having 1 to 4 carbon atoms such as methanol, ethanol, etc., ketones having 3 to 6 carbon atoms such as acetone, methyl ethyl ketone, etc., nitrites having 2 to 5 carbon atoms such as acetonitrile, propionitrile, etc., amides such as formamide, N,N-dimethylformamide, etc., ethers such as dioxane, tetrahydrofuran, etc., polar solvents such as dimethylsulfoxide, sulfolane, hexamethylphosphoramide, etc. These solvents can be used alone or in combination thereof. Among them, water, methanol or a mixed solvent of water and acetonitrile is preferable.

The solvent is usually used in an amount of about 2 to 100 times by weight of Compound (II). It is preferable to use a mixed solvent of water and acetonitrile in the present reaction since only the small amount of by-product forms. In this case, the amount of acetonitrile is usually 2 to 10 times by weight and preferably 4 to 6 times by weight of Compound (II).

Though methylamine or a salt thereof can be used in an amount of 1 to a large excess amount based on Compound (II), it is preferable to use methylamine or a salt thereof in an amount of 10 to 100 moles per mole of Compound (II). The reaction temperature is usually from −10 to 25° C., preferably from about 5 to 25° C.

Though the reaction time varies depending on the used amount of methylamine or a salt thereof and reaction temperature, it is usually from 30 minutes to 48 hours, preferably from 2 to 5 hours.

In the reaction, methylamine may be used as a form of salt. In this case a base is used in order to convert the salt to free methylamine. Such bases include inorganic base, such $C_{1-6}$alkyl or aryl lithiums as methyl lithium, ethyl lithium, n-butyl lithium, sec-butyl lithium, tert-butyl lithium, phenyl lithium, etc., such lithium alkyl amides having 2 to 6 carbon atoms as lithium dimethylamide, lithium diethylamide, lithium diisopropylamide, etc., such metal hydrides as lithium hydride, sodium hydride, etc., such alkali metal alkoxides having 1 to 6 carbon atoms as lithium ethoxide, lithium tert-butoxide, sodium methoxide, sodium ethoxide, potassium tert-butoxide, sodium tert-butoxide, etc., such alkali metal amides as lithium amide, potassium amide, sodium amide, etc., such alkali metal hydroxides as lithium hydroxide, potassium hydroxide, sodium hydroxide, etc., such alkali metal carbonate or bicarbonates as sodium carbonate, potassium carbonate, sodium hydrogencarbonate, etc., organic bases such tertiary amines as triethylamine, tri(n-propyl)amine, tri(n-butyl)amine, diisopropylethylamine, cyclohexyldimethylamine, pyridine, lutidine, γ-collidine, N,N-dimethylaniline, N-methylpiperidine, N-methylpyrrolidine, N-methylmorpholine, etc. The amount used of the base is a sufficient amount to convert a salt of methylamine to free methylamine, i.e. a molar equivalent or more relative to the salt of methylamine.

A compound of the formula (I) produced in the reaction can be converted to the salt mentioned above, and a salt of a compound of the formula (I) can be converted to the compound of the formula (I).

A compound of the formula (I) or a salt thereof ( sometimes hereinafter referred to as Compound (I)) can be isolated or purified from the reaction mixture by means of a commonly known means such as extraction, concentration, neutralization, filtration, recrystallization, column chromatography, thin layer chromatography, etc.

The reaction between a compound of the formula (III) or a salt thereof (sometimes hereinafter referred to as Compound (III)) and guanidine or a salt thereof is carried out in a secondary or tertiary alcohol. The tertiary alcohols include one having 4 to 7 carbon atoms, for example, tert-butanol (2-methyl-2-propanol), tert-amylalcohol (2-methyl-2-butanol), 2,3-dimethyl-2-butanol, 2-methyl-2-pentanol, 3-methyl-3-pentanol, 1-methylcyclopropanol, 1-methylcyclobutanol, 1-methylcyclopentanol, 1-methylcyclohexanol, etc. The secondary alcohols includes one having 3 to 7 carbon atoms, for example, isopropyl alcohol, 2-butanol, 2-pentanol, 3-pentanol, 3-methyl-2-butanol, cyclopropanol, cyclobutanol, cyclopentanol, cyclohexanol, etc. These can be used in combination of two or more. Among them, tertiary alcohol is preferable and tert-butanol is the most preferable.

The amount of a solvent is usually 1 to 100 times by weight and preferably 1 to 5 times by weight of Compound (III).

The amount of guanidine or a salt thereof is usually an equivalent or more, preferably 1 to 10 moles, the most preferably 3 to 6 moles relative to Compound (III). The reaction temperature is usually 0 to 40° C., preferably 0 to 30° C. It is not preferable that the reaction temperature is higher than the range, since Compound (II) accompanies isomerization. The reaction may be carried out in the presence of a base. The bases include inorganic base, such $C_{1-6}$alkyl or aryl lithiums as methyl lithium, ethyl lithium, n-butyl lithium, sec-butyl lithium, tert-butyl lithium, phenyl lithium, etc., such lithium alkyl amides having 2 to 6 carbon atoms as lithium dimethylamide, lithium diethylamide, lithium diisopropylamide, etc., such metal hydrides as lithium hydride, sodium hydride, etc., such alkali metal alkoxides having 1 to 6 carbon atoms as lithium ethoxide, lithium tert-butoxide, sodium methoxide, sodium ethoxide, potassium tert-butoxide, sodium tert-butoxide, etc., such alkali metal amides as lithium amide, potassium amide, sodium amide, etc., such alkali metal hydroxides as lithium hydroxide, potassium hydroxide, sodium hydroxide, etc., such alkali metal carbonate or bicarbonates as sodium carbonate, potassium carbonate, sodium hydrogencarbonate, etc., organic bases such tertiary amines as triethylamine, tri(n-propyl)amine, tri(n-butyl)amine, diisopropylethylamine, cyclohexyldimethylamine, pyridine, lutidine, γ-collidine, N,N-dimethylaniline, N-methylpiperidine, N-methylpyrrolidine, N-methylmorpholine, etc.

In the reaction, guanidine is used usually as a form of salt. In this case a base is used in order to convert the salt to free guanidine. The bases include those mentioned above. The used amount of the base is a sufficient amount to convert a salt of guanidine to free guanidine, i.e. a molar equivalent or more relative to the salt of guanidine.

Though the reaction time varies depending on the kind of Compound (III), the kind and amount of guanidine or a salt thereof, the kind or amount of base, the kind of solvent, reaction temperature, etc., it is usually 30 minutes to 120 hours, preferably 1 to 24 hours.

As the combination of a solvent and a base, it is preferable to use a combination of tert-butanol and an alkali metal tert-butoxide, especially a combination of potassium tert-butoxide and sodium tert-butoxide.

In order to prevent hydrolysis of the ester, water contained in the reaction system may be removed by adding a drying agent, which does not affect to the reaction, such as Molecular sieves, etc. A compound of the formula (II) can be converted to a salt of the compound, and a salt of a compound of the formula (II) can be converted to a compound of the formula (II).

Compound (II) can be isolated or purified from the reaction mixture by means of a commonly known means such as extraction, concentration, neutralization, filtration, recrystallization, column chromatography, thin layer chromatography, etc.

Compound (II) can be used without isolation and purification in the next reaction i.e. the reaction between Compound (II) with methylamine or a salt thereof.

Compound (III) can be produced, for example, by reacting a compound of the formula:

(IV)

(wherein $R^1$ has the same meaning as defined above) or a salt thereof (sometimes hereinafter referred to as Compound (IV)) with a compound of the formula:

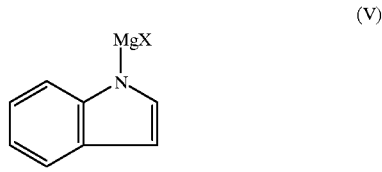

(V)

(wherein X is a halogen atom.)(sometimes hereinafter referred to briefly as Compound (V)).

In the formula (V), a halogen atom represented by X includes chlorine, bromine, iodine, fluorine. Among them, chlorine, bromine and iodine are preferable.

Compound (IV) can form salts when $R^1$ is a hydrogen atom. The salts include, inorganic base salt, organic base salt, etc. As a base which forms the base salt, those of Compound (III) may be mentioned.

The reaction between Compound (IV) and Compound (V) is usually carried out in a solvent. The solvent includes, for example, ethers such as diethyl ether, tert-butylmethyl ether, diisopropyl ether, anisole, etc., aliphatic halogenated hydrocarbons such as dichloromethane, dicholoroethane, chloroform, carbon tetrachloride, etc., hydrocarbons such as n-hexane, benzene, toluene, etc.

These solvents can be used alone or in combination thereof. Among them, a mixed solvent of diethyl ether and dichloromethane and a mixed solvent of tert-butylmethyl ether and dichloromethane are preferable.

The solvent is usually used in an amount of 5 to 100 times by weight, preferably 10 to 20 times by weight of Compound (IV). Compound (V) is usually used in an amount of 1 to 3 moles, preferably 1.5 to 2.5 moles per mole of Compound (IV). The reaction temperature is usually from −50 to 25° C., preferably from about −30 to 0° C.

Though the reaction time varies depending on the reaction temperature, etc., it is, for example, one minute to 15 hours when the reaction temperature is −50 to 25° C., and one minute to 3 hours when the reaction temperature is −30 to 0° C.

Compound (III) can be isolated or purified from the reaction mixture by means of a commonly known means such as extraction, concentration, neutralization, filtration, recrystallization, distillation, column chromatography, thin layer chromatography, etc.

The compound of the formula (III) produced in the reaction can be converted to the salt mentioned above in the usual way, and the salt of a compound of the formula (III) can be converted to a compound of the formula (III). Compound (III) can be hydrolyzed to give a free carboxylic acid in the usual way. The free acid can be esterified to give Compound (III) in the usual way. For example, Compound (III) may be hydrolyzed to give the free acid in a known method, and after purification such as extraction or recrystallization, the free acid may be esterified to give Compound (III) by a known method. In this case, Compound (III) obtained may be the same or different from Compound (III) which was hydrolyzed.

Compound (IV) can be synthesized, for example, by a method described in Tetrahedron Letters, 36, 2063(1995) or Journal of Organic Chemistry, 56, 2869(1991) or a method based thereon. Compound (V) can be synthesized by a method described in Journal of American Chemical Society (J. Am. Chem. Soc.), 81, 163 (1959) or a method based thereon.

Best Mode for Carrying Out the Invention

The present invention is hereinafter described in more detail by means of, but not limited to, the following working examples. In the following Examples, "room temperature" means "about 15~30° C."

Reference Example 1

Production of ethyl (2RS,3SR)-2-hydroxy-3-(indol-3-yl) butanoate

Under argon atmosphere, to a mixture of magnesium (2.50 g) and iodine (10 mg) was added tert-butylmethyl ether (5 ml). To the mixture was added a solution of bromoethane (16.8 g) in tert-butylmethyl ether (25 ml) over a period of 2 hours. The mixture was stirred for 1 hour at 40° C., whereby a solution of ethyl magnesium bromide in tert-butylmethyl ether was obtained. 2.4 M of ethyl magnesium bromide was confirmed by titration.

Indole (1.15 g) was dissolved in dichloromethane (2 ml), and to the mixture was added dropwise a 2.4 M solution of ethyl magnesium bromide in tert-butylmethyl ether (4.2 ml) over a period of 30 minutes under ice cooling. After the addition, the mixture was stirred for 30 minutes at 0° C. While cooling the mixture at −30° C., a solution of ethyl (2RS,3SR)-2,3-epoxybutanoate (500 mg) in dichloromethane (3 ml) was added dropwise over the period of 20 minutes. The mixture was stirred for 2 hours at −30~−10° C. To the mixture were added a saturated aqueous solution of ammonium chloride (20 ml), and 1 N hydrochloric acid (10 ml). The mixture was extracted with dichloromethane (20 ml×2). The organic layers were combined, washed with saturated sodium chloride aqueous solution (20 ml) and dried over anhydrous magnesium sulfate. The organic layer was concentrated under reduced pressure, and the residue was subjected to silica gel column chromatography (70–230 mesh: 34 g ). Fraction eluted with hexane-ethyl acetate (3:1) was collected. The fraction was concentrated under reduced pressure, whereby ethyl (2RS,3SR)-2-hydroxy-3-(indol-3-yl) butanoate (629 mg) was obtained as pale brown oily substance. The yield from ethyl (2RS,3SR)-2,3-epoxybutanoate was 66%.

$^1$H-NMR (CDCl$_3$) δ ppm: 1.27 (3H, t, J=7.4 Hz), 1.34 (3H, d, J=7.0 Hz), 2.75 (1H, d, J=5.6 Hz), 3.63 (1H, dq, J=7.0, 3.2 Hz), 4.25(2H, q, J=7.4 Hz), 4.48(1H, dd, J=5.6, 3.2 Hz), 7.0–7.3(3H, m), 7.37(1H, d, J=7.4 Hz), 7.68(1H, d, J=7.4 Hz), 8.05(1H, bs)

Reference Example 2

The production of ethyl (2RS,3SR)-2-hydroxy-3-(indol-3-yl) butanoate

Under argon atmosphere, to a mixture of magnesium (235 mg) and iodine (5 mg) was added anisole (1 ml). To the mixture was added dropwise iodoethane (1.56 g). The mixture was stirred for 30 hours at room temperature and further for 1 hour at 55° C., whereby, a solution of ethyl magnesium iodide in anisole was obtained. Under ice cooling, to the mixture was added dropwise a solution of indole (560 mg) in dichloromethane (3 ml). After the addition was completed, the mixture was stirred for 30 minutes at room temperature. While cooling the mixture at −10° C., solution of ethyl (2RS,3SR) -2,3-epoxybutanoate (501 mg) in dichloromethane (2 ml) was added dropwise. After the mixture was stirred for 2 hours at −10~−4° C., to the mixture was added 1 N hydrochloric acid (20 ml). The mixture was extracted twice with dichloromethane (10 ml). The organic layers were combined, washed with saturated solution of sodium chloride (10 ml), dried over anhydrous magnesium sulfate and concentrated under reduced pressure. The residue was subjected to silica gel column chromatography (70–230 mesh: 40 g). The fraction eluted with hexane-ethyl acetate (3:1) were collected and concentrated under reduced pressure, whereby ethyl (2RS,3SR)-2-hydroxy-3-(indol-3-yl) butanoate (387 mg) was obtained as pale brown oily substance. The yield from ethyl (2RS,3SR)-2,3-epoxybutanoate was 40%. The product is identical with the compound obtained in Reference Example 1 in $^1$H-NMR (CDCl$_3$).

Reference Example 3

The production of ethyl (2RS,3SR)-2-hydroxy-3-(indol-3-yl) butanoate

Under argon atmosphere, to a mixture of magnesium (235 mg) and iodine (5 mg) was added diisopropyl ether (1.5 ml). To the mixture was added dropwise iodoethane (2.34 g). After the mixture was stirred for 30 minutes at room temperature, a solution of indole (561 mg) in dichloromethane (2 ml) was added dropwise under ice cooling. After the addition was completed, the mixture was stirred for 30 minutes at room temperature. To the solution was added dropwise a solution of ethyl (2RS,3SR)-2,3-epoxybutanoate (500 mg) in dichloromethane (2 ml) under cooling at −10° C. After the mixture was stirred for 3 hours at −10 to −5° C., 1 N hydrochloric acid (20 ml) was added. The mixture was extracted twice with dichloromethane (10 ml). The organic layers were combined, washed with saturated solution of sodium chloride (10 ml), dried over anhydrous magnesium sulfate and concentrated under reduced pressure. The residue was subjected to silica gel column chromatography (70–230 mesh: 20 g). The fraction eluted with hexane-ethyl acetate (2:1) was collected and concentrated under reduced pressure, whereby, ethyl (2RS,3SR)-2-hydroxy-3-(indol-3-yl) butanoate (274 mg) was obtained as pale brown oily substance. The yield from ethyl (2RS,3SR) -2,3-epoxybutanoate was 29%. The product was identical with the compound obtained in Reference Example 1 in $^1$H-NMR (CDCl$_3$).

Reference Example 4

The production of ethyl (2RS,3SR)-2-hydroxy-3-(indol-3-yl) butanoate

Indole (5.86 g) was dissolved in dichloromethane (50 ml) and to the solution was added dropwise 2.89 M solution of methyl magnesium bromide in diethyl ether (40 ml) over a period of 45 minutes at room temperature. After the dropwise addition was completed, the mixture was stirred for 45 minutes at room temperature. Under cooling at −10° C., a solution of ethyl (2RS,3SR)-2,3-epoxybutanoate (6.51 g) in dichloromethane (50 ml) was added dropwise over a period of 20 minutes. The mixture was stirred for 1 hour at −10 ° C. To the mixture was added 1 N aqueous solution of hydrochloric acid (150 ml). The organic layer was removed, and the aqueous layer was extracted with dichloromethane (50 ml). The organic layers were combined, and concentrated under reduced pressure. The residue was dissolved by adding ethanol (56 ml) and water (24 ml). To the solution was added 1 N aqueous solution of sodium hydroxide (50 ml) under ice cooling. The mixture was stirred for 3.5 hours under ice cooling and 12 hours at room temperature. To the mixture was added 1 N aqueous solution of sodium hydroxide (25 ml), and the mixture was stirred for 1 hour at room temperature. The ethanol was distilled off under reduced pressure, and aqueous layer was washed twice with ethyl acetate (70 ml). The aqueous layer was acidified by adding conc. hydrochloric acid (10 ml). The mixture was extracted twice with ethyl acetate (100 ml). The ethyl acetate layers were combined and dried over anhydrous magnesium sulfate. To the ethyl acetate layer was added activated carbon (1 g) and mixture was stirred. After filtration, the filtrate was concentrated under reduced pressure. The residue was recrystallized from water to give (2RS,3SR)-2-hydroxy-3-(indol-3-yl)butyric acid (7.27 g) as pale brown solid.

Under ice cooling, acetyl chloride (23.6 ml) was gradually added to ethanol (122 ml). The mixture was stirred for 1 hour under ice cooling, and to the mixture was added (2RS,3SR)-2-hydroxy-3-(indol-3-yl)butyric acid (7.27 g). The mixture was stirred for 16 hours at room temperature and concentrated under reduced pressure. To the residue was added ethyl acetate (200 ml), and the mixture was washed twice with saturated aqueous solution of sodium hydrogencarbonate (50 ml), water (35 ml), saturated sodium chloride solution (30 ml) successively, and dried over anhydrous magnesium sulfate. The mixture was concentrated under reduced pressure to give ethyl (2RS,3SR)-2-hydroxy-3-(indol-3-yl) butanoate (7.96 g) as a brown oily substance. The yield from ethyl (2RS,3SR)-2,3-epoxybutanoate was 64%. The product was identical with the compound obtained in Reference Example 1 in $^1$H-NMR (CDCl$_3$).

Reference Example 5

The production of ethyl (2S,3R)-2,3-epoxybutanoate

AD-mix-β [Produced by ALDRICH company] (213 g) was added to a mixture of tert-butanol (760 ml) and water (760 ml). To the mixture was added methanesulfonamide (14.5 g). Under ice cooling, ethyl crotonate (17.4 g) was added, and the mixture was stirred for 5 hours at 0 to 6° C. and 25 hours at room temperature. Sodium sulfite (225 g) was added and the mixture was stirred for 1 hour. The mixture was extracted with ethyl acetate (1 litter)for 22 hours by using liquid-liquid extraction apparatus. The ethyl acetate layer was taken, dried over anhydrous magnesium sulfate and concentrated under reduced pressure. To the residue was added diethyl ether (300 ml), and insolubles were filtered off. The filtrate was concentrated under reduced pressure. To the residue was added 30% a solution of hydrogen bromide in acetic acid (125 ml), and the mixture was stirred for 1 hour at 45° C. After the mixture was cooled to room temperature, ethanol (280 ml) was added. The mixture was stirred for 21 hours at 45° C. and poured into a mixture of sodium hydrogencarbonate (168 g) and water (500 ml) under ice cooling with cautiously. The mixture was extracted five times with diethylether (200 ml). The organic layers were combined, dried over anhydrous magnesium sulfate and concentrated under reduced pressure. The residue was dissolved in dichloromethane (200 ml). To the solution was added DBU (23.4 g). The mixture was stirred for 1 hour at room temperature, diluted with dichloromethane (300 ml) and washed with water (100 ml) and 0.5 N hydrochloric acid (200 ml). The aqueous layer was extracted twice with dichloromethane (50 ml). The dichloromethane layers were combined, and to the layer was added triethylamine (1 ml). The mixture was dried over anhydrous magnesium sulfate and concentrated under reduced pressure. The residue was subjected to distillation under reduced pressure to give ethyl (2S,3R)-2,3-epoxybutanoate (10.0 g) as colorless liquid (Yield: 50%). Optical purity based on the analysis of HPLC of the product was 95% ee.

Boiling point: 68–70° C./15 mmHg

Reference Example 6

The production of ethyl (2S,3R)-2-hydroxy-3-(indol-3-yl)butanoate

Indole (1.0 g) was dissolved in dichloromethane (4 ml), and to the mixture was added dropwise a solution of 3.35 M methyl magnesium bromide in diethyl ether (6.4 ml) over the period of 30 minutes under ice cooling. After the dropwise addition was completed, the mixture was stirred for 40 minutes at room temperature. To the mixture was added dropwise a solution of ethyl (2S,3R)-2,3-epoxybutanoate (2.22 g) in dichloromethane (8 ml) over a period of 1.5 hours under cooling at −30° C. The mixture was stirred for 30 minutes at −25~30° C., and saturated aqueous solution of ammonium chloride (40 ml) and 1 N hydrochloric acid (25 ml) were added. The mixture was extracted three times with dichloromethane (20 ml). The organic layers were combined, dried over anhydrous magnesium sulfate and concentrated under reduced pressure.

The residue was subjected to silica gel column chromatography (70–230 mesh: 60 g ). The fractions eluted with hexane-ethyl acetate (3:1) were collected and concentrated under reduced pressure, whereby ethyl (2S,3R)-2-hydroxy-3-(indol-3-yl) butanoate (1.53 g) was obtained as a pale brown oily substance. Yield from indole was 72%.

$^1$H-NMR(CDCl$_3$) δ ppm: 1.27(3H, t, J=7.4 Hz), 1.34(3H, d, J=7.0 Hz), 2.75(1H, d, J=5.6 Hz), 3.63(1H, dq, J=7.0, 3.2 Hz), 4.25(2H, q, J=7.4 Hz), 4.48(1H, dd, J=5.6, 3.2 Hz), 7.0–7.3(3H, m), 7.37(1H, d, J=7.4 Hz), 7.68(1H, d, J=7.4 Hz), 8.05(1H, bs)

EXAMPLE 1

The production of (5S)-2-amino-5-[(1R)-1-(indol-3-yl)ethyl]-4-oxazolone

Hydrochloric acid salt of guanidine (3.34 g) was suspended in tert-butanol (16 ml). To the suspension were added potassium tert-butoxide (4.21 g) and Molecular sieves 4 Å (12 g). The mixture was stirred for 3 days at room temperature. A solution of Ethyl (2S,3R)-2-hydroxy-3-(indol-3-yl) butanoate (1.52 g) in tert-butanol (14 ml) was added. The mixture was stirred for 6 hours at room temperature. The reaction mixture was poured into an aqueous solution of ammonium chloride containing ice (100 ml) and insoluble materials were filtered off. The insoluble materials were washed twice with ethyl acetate-tetrahydrofuran (8:1) (90 ml). Filtrate and washings were combined and the mixed solution was washed with saturated sodium hydrogencarbonate (20 ml), water (50 ml) and saturated aqueous solution of sodium chloride (50 ml) successively, and dried over anhydrous magnesium sulfate. The solution was concentrated under reduced pressure, and to the residue was added ethyl acetate (3 ml). The solid substance was harvested by filtration, washed twice with ethyl acetate (2 ml) and dried, whereby (5S)-2-amino-5-[(1R)-1-(indol-3-yl)ethyl]-4-oxazolone (1.23 g) as white crystals (Yield: 82%).

$^1$H-NMR(DMSO-d$_6$) δ ppm: 1.20(3H, d, J=7.4 Hz), 3.57 (1H, dq, J=7.4, 2.6 Hz), 4.91 (1H, d, J=2.6 Hz), 6.94–7.16 (3H,m), 7.35(1H, d, J=7.2 Hz), 7.58(1H, d, J=7.4 Hz), 8.25(1H, bs), 8.30(1H, s), 8.41(1H, bs)

EXAMPLE 2

The production of indolmycin (5S)-2-Amino-5-[(1R)-1-(indol-3-yl)ethyl]-4-oxazolone (1.22 g) was dissolved in 40% aqueous solution of methylamine (9 ml). The vessel was stoppered and kept standing for 3 hours at 5° C. The reaction mixture was concentrated under reduced pressure to make the volume to about half. The precipitated solid substance was collected by filtration and washed with water (20 ml). The solid substance was recrystallized from methanol-water to give indolmycin (0.777 g) as white crystals (yield: 60%).

$^1$H-NMR(DMSO-d$_6$) δ ppm: 1.19 & 1.25(total 3H, d, J=7.0 Hz), 2.7–2.82(3H, m), 3.59 (1H, m), 4.90 & 4.94(1H, d, J=2.4 Hz), 6.95–7.19(3H, m), 7.35(1H, d, J=7.8 Hz), 7.58 (1H, d, J=7.8 Hz), 8.30(1H, s), 8.64(1H, bs) IR(KBr)ν cm$^{-1}$: 3266, 1730, 1604

Industrial Applicability

According to the present invention, indolmycin can be produced in an optically active form in a high yield and high quality as compared to the known methods. The process of the present invention can be safely carried out in a conventional manner and it is advantageous from the industrial point of view.

What is claimed is:

1. A process for producing a compound of the formula:

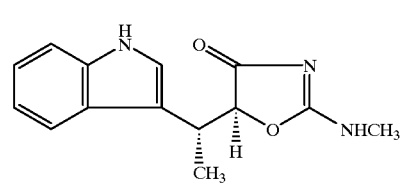

(I)

or a salt thereof, which comprises reacting a compound of the formula:

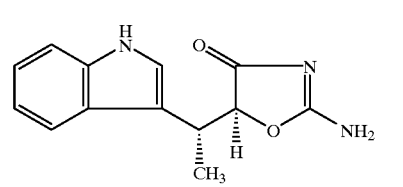

(II)

or a salt thereof with methylamine or a salt thereof.

2. A process as claimed in claim 1, wherein the reaction is carried out in a mixed solvent of water and acetonitrile.

* * * * *